United States Patent [19]

Uhr et al.

[11] Patent Number: 6,075,019
[45] Date of Patent: Jun. 13, 2000

[54] ARYLTHIO-DITHIAZINDIOXIDES AND THEIR USE AS PESTICIDES

[75] Inventors: Hermann Uhr, Krefeld; Martin Kugler, Leichlingen; Peter Wachtler, Krefeld, all of Germany

[73] Assignee: Bayer Aktiengesellschaft, Leverkusen, Germany

[21] Appl. No.: 09/331,676

[22] PCT Filed: Dec. 22, 1997

[86] PCT No.: PCT/EP97/07242

§ 371 Date: Jun. 23, 1999

§ 102(e) Date: Jun. 23, 1999

[87] PCT Pub. No.: WO98/29400

PCT Pub. Date: Jul. 9, 1998

[30] Foreign Application Priority Data

Jan. 3, 1997 [DE] Germany ............................ 197 00 062

[51] Int. Cl.[7] ...................... C07D 285/15; C07D 417/00; A01N 43/88
[52] U.S. Cl. ............................................. 514/222.5; 544/5
[58] Field of Search ............................... 544/5; 514/222.5

[56] References Cited

U.S. PATENT DOCUMENTS 4,017,638   4/1977   Dittrich et al. ..................... 424/326

FOREIGN PATENT DOCUMENTS 195 32 061   3/1997   Germany.
195 45 635   6/1997   Germany.
197 00 062   1/1999   Germany.

OTHER PUBLICATIONS

Bull. of the Chem. Soc. of Japan, vol. 45, (month unavailable) 1972, pp. 3217–3218 Nakahashi et al.

Bull. of the Chem. Soc. of Japan, vol. 45, (month unavailable) 1972, pp. 1567–1568 Hasegawa et al.

*Primary Examiner*—Mukund J. Shah
*Assistant Examiner*—Hong Liu
*Attorney, Agent, or Firm*—Joseph C. Gil; Carol Marmo

[57] ABSTRACT

The invention relates to novel S-aryl-dithiazine dioxides, to processes for their preparation and to the use in crop protection and in the protection of materials.

12 Claims, No Drawings

ARYLTHIO-DITHIAZINDIOXIDES AND THEIR USE AS PESTICIDES

This application is a 371 of PCT/EP97/07242, filed on Dec. 22, 1997.

TECHNICAL FIELD OF THE INVENTION

The invention relates to novel S-aryl-dithiazine dioxides, to processes for their preparation and to the use in crop protection and in the protection of materials.

BACKGROUND OF THE INVENTION

Dithiazine dioxides having alkyl substitution at the S have already been described, a biological activity has not been mentioned (see Nakahashi, K. et al., Bull. Chem. Soc. Jpn. 45, 3217 (1972); Masegawa, K. et al., Bull. Chem. Soc. Jpn. 45, 1567 (1972)).

DETAILED DESCRIPTION OF THE INVENTION

Surprisingly, it has now been found that the novel compounds of the general formula (I)

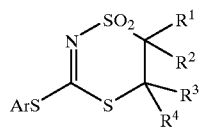

(I)

in which

R$^1$, R$^2$, R$^3$, R$^4$ independently of one another each represent hydrogen, optionally substituted alkyl, alkenyl, alkinyl or aryl and Ar represents optionally substituted aryl are outstandingly suitable for the protection of plants and materials.

The formula (I) provides a general definition of the compounds according to the invention. Preference is given to compounds of the formula (1) in which R$^1$, R$^2$, R$^3$ and R$^4$ independently of one another each represent hydrogen, straight-chain and branched alkyl having 1 is 10 carbon atoms, straight-chain or branched alkenyl having 2 to 10 carbon atoms or straight-chain or branched alkinyl having 2 to 10 carbon atoms, which is optionally mono- to polysubstituted by identical or different substituents selected from the group consisting of halogen, alkoxy having 1 to 6 carbon atoms, halogenoalkoxy having 1 to 6 carbon atoms and 1 to 9 identical or different halogen atoms, alkylthio having 1 to 6 carbon atoms, halogenoalkylthio having 1 to 6 carbon atoms and 1 to 9 identical or different halogen atoms, acyl having 1 to 6 carbon atoms, acyloxy having 1 to 6 carbon atoms, (alkoxy)carbonyl having 1 to 6 carbon atoms, amino, which is optionally substituted by identical or different substituents selected from the group consisting of alkyl and aryl, optionally substituted phenoxy, aryl, pyridyl or pyridyloxy, nitro or cyano, or represent aryl, which is optionally mono- to pentasubstituted by halogen, alkyl having 1 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino having straight-chain or branched alkyl radicals having to 1 to 6 carbon atoms, dialkylamino having identical or different, straight-chain or branched alkyl radicals having in each case 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano and Ar represents aryl, which is optionally mono- to pentasubstituted by halogen, alkyl having 1 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino having straight-chain or branched alkyl radicals having 1 to 6 carbon atoms, dialkylamino having identical or different, straight-chain or branched alkyl radicals having in each case 1 to 6 carbon atoms, cycloalkyl having to 1 to 6 carbon atoms, methylenedioxy, difluoromethylenedioxy, chlorofluoromethylenedioxy, dichloromethylenedioxy, nitro or cyano.

Particular preference is given to compounds of the formula (I) in which

R$^1$, R$^2$, R$^3$ and R$^4$ independently of one another each represent hydrogen, straight-chain or branched alkyl having 1 to 8 carbon atoms, straight-chain or branched alkenyl having 2 to 8 carbon atoms or straight-chain or branched alkinyl having 2 to 8 carbon atoms, which is optionally mono- to tetrasubstituted by identical or different substituents selected from the group consisting of fluorine, chlorine, alkoxy having 1 to 5 carbon atoms, halogenoalkoxy having 1 to 5 carbon atoms and 1 to 5 fluorine and/or chlorine atoms, alkylthio having 1 to 5 carbon atoms, halogenoalkylthio having 1 to 5 carbon atoms and 1 to 5 fluorine and/or chlorine atoms, acyl having 1 to 5 carbon atoms, acyloxy having 1 to 5 carbon atoms, alkoxycarbonyl having 1 to 5 carbon atoms, amino, which is optionally substituted by identical or different substituents selected from the group consisting of alkyl having 1 to 4 carbon atoms and phenyl, optionally substituted phenoxy, aryl, pyridyl, pyridyloxy, nitro or cyano, or represent phenyl, which is optionally mono- to tetrasubstituted by fluorine, chlorine, alkyl having 1 to 8 carbon atoms, halogenoalkyl having 1 to 6 carbon atoms and 1 to 6 fluorine and/or chlorine atoms, alkoxy having 1 to 8 carbon atoms, halogenoalkoxy having 1 to 6 carbon atoms and 1 to 6 fluorine and/or chlorine atoms, alkylthio having 1 to 8 carbon atoms, halogenoalkylthio having 1 to 6 carbon atoms and 1 to 6 fluorine and/or chlorine atoms, amino, monoalkylamino having alkyl radicals of 1 to 4 carbon atoms, dialkylamino having identical or different alkyl radicals having in each case 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano, and Ar represents phenyl, which is optionally mono- to tetrasubstituted, preferably mono- to disubstituted, by fluorine, chlorine, bromine, alkyl having 1 to 8 carbon atoms, such as preferably methyl, ethyl, n- or i-propyl, n-, i-, s- or t-butyl, halogenoalkyl having 1 to 6 carbon atoms and 1 to 6 fluorine and/or chlorine atoms, such as preferably trifluoromethyl, trifluoroethyl, difluorochloromethyl, alkoxy having 1 to 8 carbon atoms, such as preferably methoxy, ethoxy, n- or i-propoxy, n-, i-, s- or t-butoxy, halogenoalkoxy having 1 to 6 carbon atoms and 1 to 6 fluorine and/or chlorine atoms, such as preferably difluoromethoxy, trifluoromethoxy, difluorochloromethoxy, trifluoroethoxy, alkylthio having 1 to 8 carbon atoms, halogenoalkylthio having 1 to 6 carbon atoms and 1 to 6 fluorine and/or chlorine atoms, amino, monoalkylamino having alkyl radicals of 1 to 4 carbon atoms, dialkylamino having identical or different alkyl radicals having in each case 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano.

$R^1$, $R^2$, $R^3$ and $R^4$ each particularly preferably represent hydrogen and/or methyl.

The particular radical definitions given for the radicals in the respective combinations or preferred combinations of radicals are, independently of the particular combination given, also replaced at will by radical definitions of other preferred ranges.

Moreover, it has been found that the compounds of the formula (I) are obtained if the salts of the general formula (II)

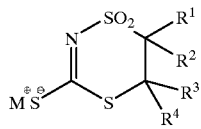

(II)

in which $R^1$, $R^2$, $R^3$ and $R^4$ are each as defined above and $M^\oplus$ represents an alkali metal ion or alkaline earth metal ion, in particular $Na^+$, $K^+$, are reacted with diazonium salts of the general formula (III)

(III)

in which

Ar is as defined above and $A^\ominus$ represents the anion of a mineral acid, in aqueous/alkaline solution, if appropriate in the presence of a catalyst.

Preferably, a base and, if appropriate, a catalyst, and then the diazonium salt solution (III) are added to a solution of (II). Preferred bases employed are alkali metal hydroxides such as, for example, potassium hydroxide or sodium hydroxide.

Suitable catalysts are all catalysts which promotes the exchange of the diazonium function for sulphur-containing radicals.

Preference is given to using Cu(I) salts or copper powder. The temperature during the addition of the diazonium salt solution can be varied within a wide range. In general, the reaction is carried out between −30° C. and +60° C., preferably between −20° C. and +40° C. The preparation of the diazonium salt solution from anilines is carried out by literature methods.

Some of the salts of the general formula (II) are known, or they can be prepared by methods similar to those known from the literature (see literature references p.1). It is possible to use either salts of the formula (II) which have been isolated in solid form, or solutions which have been prepared in situ.

The active compounds according to the invention have a strong microbicidal action and can be used for controlling undesirable microorganisms, preferably fungi and bacteria, in crop protection and in the protection of materials.

In the present context, the term industrial materials refers to non-living materials which have been prepared for use in industry. Possible examples are industrial materials which are to be protected by active compounds according to the invention against microbial alteration or destruction, adhesives, sizes, paper and card, textiles, leather, wood, coating compositions and plastics articles, cooling lubricants and other materials which can be attacked or decomposed by microorganisms. In the context of the materials to be protected mention may also be made of parts of production plants, for example cooling water circuits, which may be adversely affected by reproduction of microorganisms. Preferred industrial materials in the context of the present invention are adhesives, sizes, papers and cards, leather, wood, coating compositions, cooling lubricants and heat transfer fluids.

Examples of microorganisms which can bring about degradation or an alteration in the industrial materials are bacteria, fungi, yeasts, algae and slime organisms. The active compounds or compositions according to the invention preferably act against bacteria, fungi, especially mould fungi, and also against slime organisms and algae.

By way of example, mention may be made of microorganisms of the following genera:

Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Fungicidal compositions in crop protection are employed for controlling Plasmodiophoromycetes, Oomycetes, Chytridiomycetes, Zygomycetes, Ascomycetes, Basidiomycetes, Deuteromycetes.

Some causative organisms of fungal diseases which come under the abovementioned generic term may be mentioned by way of example, but not by way of limitation:

Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubense*;
Plasmopara species, such as, for example, *Plasmopara viticola*;
Peronospora species, such as, for example, *Peronospora pisi* or *Peronospora brassicae*;
Erysiphe species, such as, for example, *Erysiphe graminis*;

Spaaerotheca species, such as, for example, *Sphaeroteca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidia form: Drechslera, synonym: Helminthosporium);

Cochliobolus species, such as, for example, *Cochliobolus sativus* (conidia form: Drechslera, synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia speciies, such as, for example, *Pellicularia sasakii;*

Pyyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The fact that the active compounds are well tolerated by plants also permits treatment of plants at the concentrations required for controlling plant diseases, it being possible to carry out treatment of above-ground parts of plants, and also treatment of planting stock and seeds and of the soil.

Depending on their respective physical and/or chemical properties, the active compounds of the formula (I) can be converted into customary formulations, such as solutions, emulsions, suspensions, powders, foams, pastes, granules, aerosols and very fine capsules in polymeric substances.

These formulations and compositions are prepared in a known manner, for example by mixing the active compounds with extenders, that is, liquid solvents, liquefied gases under pressure, and/or solid carriers, if appropriate with the use of surfactants, that is, emulsifiers and/or dispersants and/or foam-formers. If the extender used is water, it is also possible to use for example organic solvents as auxiliary solvents. Essentially, suitable liquid solvents are: aromatics, such as xylene, toluene and alkylnaphthalenes, chlorinated aromatics or chlorinated aliphatic hydrocarbons, such as chlorobenzenes, chloroethylenes, or methylene chloride, aliphatic hydrocarbons, such as cyclohexane or paraffins, for example mineral oil fractions, alcohols, such as butanol or glycol and their ethers and esters, ketones, such as acetone, methyl ethyl ketone, methyl isobutyl ketone or cyclohexanone, strongly polar solvents, such as dimethylformamide or dimethyl sulphoxide, and water; by liquefied gaseous extenders or carriers are meant liquids which are gaseous at ambient temperature and under atmospheric pressure, for example aerosol propellants, such as halogenated hydrocarbons and butane, propane, nitrogen and carbon dioxide; suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foamformers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol, polyvinyl acetate, and natural phospholipids, such as cephalins and lecithins, and synthetic phospholipids, can be used in the formulations. Possible further additives are mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The efficacy and the activity spectrum of the active compounds of the formula (I) and of the compositions preparable therefrom, of precursors or of formulations in general can be increased by adding, if appropriate, further antimicrobial compounds, fungicides, bactericides, herbicides, insecticides or other active compounds, so as to widen the spectrum of activity or to obtain particular effects such as, for example, additional protection against insects. These mixtures may have a wider activity spectrum than the compounds according to the invention.

In many cases, synergistic effects are obtained, i.e. the activity of the mixture is greater than the activity of the individual components. Particularly suitable co-components are, for example, the following compounds:

Triazoles, such as:
azocyclotin, bitertanol, bromuconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazol, penconazole, propioconazole, (±)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, tetraconazole, triadimefon, triadimenol, triapenthenol, triflumizole, triticonazole, uniconazole and their metal salts and acid adducts;

Imidazoles, such as:
clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chlorophenoxy)-3,3-dimethylbutan-2-one and their metal salts and acid adducts;

Pyridines and pyrimidines, such as:
ancymidol, buthiobate, fenarimol, nuarimol, triamirol;

Succinate dehydrogenase inhibitors, such as:
benodanil, carboxim, carboxim sulphoxide, cyclafluramid, fenfuram, flutanil, furcarbanil, furmecyclox, mebenil, mepronil, methfuroxam, metsulfovax, pyrocarbolid, oxycarboxin, shirlan, seedvax;

Naphthalene derivatives, such as:
  terbinafine, naftifine, butenafine, 3-chloro-7-(2-aza-2,7,7-trimethyl-oct-3-en-5-ine);
Sulfenamides, such as:
  dichlorfluanid, tolylfluanid, folpet, fluorfolpet; captan, captofol;
Benzimidazoles, such as:
  carbendazim, benomyl, fuberidazole, thiabendazole or their salts;
Morpholine derivatives, such as:
  aldimorph, dimethomorph, dodemorph, falimorph, fenpropidin fenpropimorph, tridemorph, trimorphamid and their arylsulphonates, such as, for example, p-toluenesulphonic acid and p-dodecylphenylsulphonic acid;
Benzothiazoles, such as:
  2-mercaptobenzothiazole;
Benzothiophene dioxides, such as:
  N-cyclohexyl-benzo[b]thiophenecarboxamide S,S-dioxide;
Benzamides, such as:
  2,6-dichloro-N-(4-trifluoromethylbenzyl)-benzamide, tecloftalam;
Boron compounds, such as:
  boric acid, boric esters, borax;
Formaldehyde
and formaldehyde-releasing compounds,
  such as:
  benzyl alcohol mono-(poly)-hemiformal, n-butanol hemiformal, dazomet, ethylene glycol hemiformal, hexa-hydro-S-triazines, hexamethylenetetramine, N-hydroxymethyl-N'-methylthiourea, N-methylolchloroacetamide, oxazolidines, paraformaldehyde, taurolin, tetrahydro-1,3-oxazine, N-(2-hydroxypropyl)-aminemethanol;
Isothiazolinones, such as:
  N-methylisothiazolin-3-one, 5-chloro-N-methylisothiazolin-3-one, 4,5-dichloro-N-octylisothiazolin-3-one, 5-chloro-N-octylisothiazolinone, N-octylisothiazolin-3-one, 4,5-trimethylene-isothiazolinones, 4,5-benzisothiazolinones;
Aldehydes, such as:
  cinnamaldehyde, formaldehyde, glutaraldehyde, β-bromocinnamaldehyde;
Thiocyanates, such as:
  thiocyanatomethylthiobenzothiazole, methylenebisthiocyanate;
Quaternary
ammonium compounds, such as:
  benzalkonium chloride, benzyldimethyltetradecylammonium chloride, benzyldimethyldodecylammonium chloride, dichlorobenzyl-dimethyl-alkyl-ammonium chloride, didecyldimethylammonium chloride, dioctyl-dimethyl-ammonium chloride, N-hexadecyl-trimethyl-ammonium chloride, 1-hexadecyl-pyridinium chloride;
Iodine derivatives, such as:
  diiodomethyl p-tolyl sulphone, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexylcarbamate, 3-iodo-2-propinyl phenylcarbamate;

Phenols, such as:
  tribromophenol, tetrachlorophenol, 3-methyl-4-chlorophenol, 3,5-dimethyl-4-chlorophenol, phenoxyethanol, dichlorophen, 2-benzyl-4-chlorophenol, 5-chloro-2-(2,4-dichlorophenoxy)-phenol, hexachlorophene, p-hydroxybenzoic ester, o-phenylphenol, m-phenylphenol, p-phenylphenol and their alkali metal and alkaline earth metal salts;
Microbicides
having an activated halogen group, such as:
  bronopol, bronidox, 2-bromo-2-nitro-1,3-propanediol, 2-bromo-4'-hydroxy-acetophenone, 1-bromo-3-chloro-4,4,5,5-tetramethyl-2-imidazoledinone, β-bromo-β-nitrostyrene, chloroacetamide, chloramine T, 1,3-dibromo-4,4,5,5-tetrametyl-2-imidazoldinone, dichloramine T, 3,4-dichloro-(3H)-1,2-dithiol-3-one, 2,2-dibromo-3-nitrile-propionamide, 1,2-dibromo-2,4-dicyanobutane, halane, halazone, mucochloric acid, phenyl(2-chloro-cyano-vinyl)sulphone, phenyl(1,2-dichloro-2-cyanovinyl)sulphone trichloroisocyanuric acid;
Pyridines, such as:
  1-hydroxy-2-pyridinethione (and its Na, Fe, Mn, Zn salts), tetrachloro-4-methylsulphonylpyridine, pyrimethanol, mepanipyrim, dipyrithion, 1-hydroxy-4-methyl-6-(2,4,4-trimethylpentyl)-2(1H)-pyridine;
Methoxyacrylates or the like, such as:
  methyl (E)-methoximino[alpha-(o-tolyloxy)-o-tolyl]acetate, (E)-2-methoxyimino-N-methyl-2-(2-phenoxyphenyl)acetamide, (E)-2-{2-[6-(2-cyanophenoxy)pyrimidin-4-yloxy]phenyl}-3-methoxyacrylate, O-methyl-2-[([3-methoximino-2-butyl)imino]oxy)o-tolyl]-2-methoximinoacetimidate,
  2-[[[1-(2,5-dimethylphenyl)ethylidene]amino]oxy]methyl]-.alpha.-(methoximino)-N-metyl-benzeneacetamide,
  alpha-(methoxyimino)-N-methyl-2-[[[1-[3-(trifluoromethyl)phenyl]ethylidene]amino]oxy]methyl]-benzeneacetamide,
  methyl alpha-(methoxyimino)-2-[[[1-[3-(trifluoromethyl)phenyl]ethylidene]amino]oxy]methyl]-benzeneacetate,
  methyl alpha-(methoxymethylene)-2-[[[1-[3-(trifluoromethyl)phenyl]ethylidene]amino]oxy]methyl]-benzeneacetate,
  2-[[[5-chloro-3-(trifluormethyl)-2-pyridinyl]oxy]methyl]-.alpha.-(methoxyimino)-N-methyl-benzeneacetamide,
  methyl 2-[[[cyclopropyl[(4-ethoxyphenyl)imino]methyl]thio]methyl]-.alpha.-(methoxyimino)benzeneacetate,
  alpha-(methoxyimino)-N-methyl-2-(4-methyl-5-phenyl-2,7-dioxa-3,6-diazaocta-3,5-dien-1-yl)-benzeneacetamide,
  methyl alpha-(methoxymethylene)-2-(4-methyl-5-phenyl-2,7-dioxa-3,6-diazaocta-3,5-dien-1-yl)-benzeneacetate,
  alpha-(methoxyimino)-N-methyl-2-[[[1-[3-(trifluoromethyl)phenyl]ethoxy]imino]methyl]-benzeneacetamide,
  2-[[(3,5-dichloro-2-pyridinyl)oxy]methyl]-.alpha.-(methoxyimino)-N-methylbenzeneacetamide,
  methyl 2-[4,5-dimethyl-9-(4-morpholinyl)-2,7-dioxa-3,6-diazanona-3,5-dien-1-yl]-.alpha.-(methoxymethylene)-benzeneacetate;
Metal soaps, such as:
  tin naphtenate, copper naphtenate, zinc naphtenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate, zinc benzoate;

Metal salts, such as:
copper hydroxycarbonate, sodium dichromate, potassium dichromate, potassium chromate, copper sulphate, copper chloride, copper borate, zinc fluorosilicate, copper fluorosilicate;

Oxides, such as:
tributyltin oxide, $Cu_2O$, CuO, ZnO;

Dithiocarbamates, such as:
cufraneb, ferban, potassium N-hydroxymethyl-N'-methyl-dithiobarbamate, Na or K dimethyldithiocarbamate, macozeb, maneb, metam, metiram, thiram, zineb, ziram;

Nitriles, such as:
2,4,5,6-tetrachloroisophthalodinitrile, disodium cyanodithioimidocarbamate;

Quinolines, such as:
8-hydroxyquinoline and their Cu salts;

Other fungicides and bactericides, such as:
5-hydroxy-2(5H)-furanone; 4,5-benzodithiazolinone, 4,5-trimethylenedithiazolinone, N-(2-p-chlorobenzoylethyl)-hexaminium chloride, 2-oxo-2-(4-hydroxy-phenyl)acethydroximic chloride, tris-N-(cyclohexyldiazeniumdioxy)-aluminium, N-(cyclohexyldiazeniumdioxy)-tributyltin or K salts, bis-N-(cyclohexyldiazenium-dioxy)copper, Ag, Zn or Cu-containing zeolites alone or enclosed in polymeric materials.

Very particularly preferred mixtures are those with azaconazole, bromuconazole, cyproconazole, dichlobutrazol, diniconazole, hexaconazole, metaconazole, penconazole, propiconazole, tebuconazole, dichlofluanid, tolylfluanid, fluorfolpet, methfuroxam, carboxin, N-cyclohexylbenzo[b]-thiophenecarboxamide S,S-dioxide, fenpiclonil, 4-(2,2-difluoro- 1,3-benzodioxol-4-yl)-1H-pyrrole-3-carbonitrile, butenafine, imazalil, N-methylisothiazolin-3-one, 5-chloro-N-methylisothiazolin-3-one, N-octylisothiazolin-3-one, dichloro-N-octylisothiazolinone, mercaptobenthiazole, thiocyanatomethylthiobenzothiazole benzisothiazolinones, N-(2-hydroxypropyl)-aminomethanol, benzyl alcohol (hemi)-formal, N-methylolchloroacetamide, N-(2-hydroxypropyl)-aminemethanol, glutaraldehyde, omadine, dimethyl dicarbonate, and/or 3-iodo-2-propinyl n-butylcarbamate.

Furthermore, in addition to the abovementioned fungicides and bactericides, highly active mixtures are also prepared with other active compounds:

Insecticides/acaricides/nematicides:
abamectin, acephat, acetamiprid, acrinathrin, alanycarb, aldicarb, aldoxycarb, aldrin, allethrin, alpha-cypermethrin, amitraz, avermectin, AZ 60541, azadirachtin, azinphos A, azinphos M, azocyclotin, *Bacillus thuringiensis*, barthrin, 4-bromo-2(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bromophos A, bromophos M, bufencarb, buprofezin, butathiophos, butocarboxin, butoxycarboxim,
cadusafos, carbaryl, carbofuran, carbophenothion, carbosulfan, cartap, quinomethionate, cloethocarb, chlordane, chlorethoxyfos, chlorfenvinphos, chlorfluazuron, chlormephos, N-[(6-chloro-3-pyridinyl)-methyl]-N'-cyano-N-methylethanimidamide, chlorpicrin, chlorpyrifos A, chlorpyrifos M, cis-resmethrin, clocythrin, cypophenothrin clofentezin, coumaphos, cyanophos, cycloprothrin, cyfluthrin, cyhalothrin, cyhexatin, cypermethrin, cyromazin,
decamethrin, deltamethrin, demeton M, demeton S, demeton-S-methyl, diafenthiuron, dialiphos, diazinon, 1,2-dibenzoyl-1(1,1-dimethyl)-hydrazine, DNOC, dichlofenthion, dichlorvos, dicliphos, dicrotophos, diflubenzuron, dimethoate, dimethyl-(phenyl)-silyl-methyl 3-phenoxybenzyl ether, dimethyl-(4-ethoxyphenyl)silylmethyl 3-phenoxybenzyl ether, dimethylvinphos, dioxathion, disulfoton,
eflusilanate, emamectin, empenthrin, endosulfan, EPN, esfenvalerate, ethiofencarb, ethion, ethofenprox, etrimphos,
fenamiphos, fenazaquin, fenbutatin oxide, fenfluthrin, fenitrothion, fenobucarb, fenothiocarb, fenoxycarb, fenpropathrin, fenpyrad, fenpyroximat, fensulfothion, fenthion, fenvalerate, fipronil, fluazuron, flucycloxuron, flucythrinate, flufenoxuron, flumethrin flufenprox, fluvalinate, fonophos, formethanate, formothion, fosmethilan fosthiazat, fubfenprox, furathiocarb,
HCH, heptenophos, hexaflumuron, hexythiazox, hydramethylnon, hydroprene,
imidacloprid, iodfenfos, iprobenfos, isazophos, isoamidophos, isofenphos, isoprocarb, isoprothiolane, isoxathion, ivermectin, lamacyhalothrin, lufenuron,
kadedrin
lambda-cyhalothrin, lufenuron,
malathion, mecarbam, mervinphos, mesulfenphos, metaldehyde, methacrifos, methamidophos, methidathion, methiocarb, methomyl, metalcarb, milbemectin, monocrotophos, moxiectin,
naled, NC 184, NI 125, nicotine, nitenpyram,
omethoate, oxamyl, oxydemethon M, oxydeprofos,
parathion A, parathion M, penfluron, permethrin, 2-(4-phenoxyphenoxy)-ethyl ethylcarbamate, phenthoat, phorat, phosalon, phosmet, phosphamidon, phoxim, pirimicarb, pirimiphos M, pirimiphos A, prallethrin, profenophos, promecarb, propaphos, propoxur, prothiophos, prothoat, pymetrozin, pyrachlophos, pyridaphenthion, pyresmethrin, pyrethrum, pyridaben, pyrimidifen, pyriproxifen,
quinalphos,
resmethrin, RH-7988, rotenone,
salithion, sebufos, silafluofen, sulfotep, sulprofos,
tau-fluvalinate, taroils, tebufenozide, tebufenpyrad, tebupirimphos, teflubenzuron, tefluthrin, temephos, terbam, terbufos, tetrachlorvinphos, tetramethrin, tetramethacarb, thiafenox, thiapronil, thiodicarb, thiofanox, thiazophos, thiocyclam, thiomethon, thionazin, thuringiensin, tralomethrin, triarathen, triazophos, triazamate, triazuron, trichlorfon, triflumuron, trimethacarb,
vamidothion, XMC, xylylcarb, zetamethrin;
Molluscicides:
fentin acetate, metaldehyde, methiocarb. niclosamide;
Herbicides and algicides
acetochlor, acifluorfen, aclonifen, acrolein, alachlor, alloxydim, ametryn, amidosulfuron, amitrole, ammonium sulphamate, anilofos, asulam, atrazine, aziptrotryne, azimsulfuron,
benazolin, benfluralin, benfuresate, bensulfuron, bensulfide, bentazone, benzofencap, benzthiazuron, bifenox, borax, bromacil, bromobutide, bromofenoxim, bromoxynil, butachlor, butamifos, butralin, butylate, bialaphos, benzoyl-prop, bromobutide, carbetamide, chlomethoxyfen, chloramben, chlorbromuron, chlorflurenol, chloridazon, chlorimuron, chlornitrofen, chloroacetic acid, chlorotoluron, chloroxuron, chlorpropham, chlorsulfuron, chlorthal, chlorthiamid, cinmethylin, cinofulsuron, clethodim, clomazone, chlomeprop, clopyralid, cyanamide, cyanazine, cycloate, cycloxydim, chloroxynil, clodinafop-propargyl, cumyluron, CGA 248757, clometoxyfen, cyhalofop, clopyrasuluron, cyclosulfamuron, dichlorprop, dichlorprop-P, diclofop, diethatyl, difenoxuron, difenzoquat, diflufenican, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn, eglinazine, endothal, EPTC, esprocarb, ethalfluralin, ethidimuron, ethofumesate, ethobenzanid, ethoxyfen, ET 751, ethametsulfuron, fenoxaprop, fenoxaprop-P, fenuron, flamprop, flamprop-M, flazasulfuron, fluazifop, fluazifop-P, fuenachlor, fluchloralin, flumeturon, fluorocglycofen, fluoronitrofen, flupropanate, flurenol, fluridone, flurochloridone, fluroxypyr, fomesafen, fosamine, flamprop-isopropyl, flamprop-isopropyl-L, flumiclorac-pentyl, flumipropyn, flumioxzim, flurtatone, flumioxzim, glyphosate, glufosinate-ammonium haloxyfop, hexazinone, imazamethabenz, isoproturon, isoxaben, isoxapyrifop, imazapyr, imazaquin, imazethapyr, ioxynil, isopropalin, imazosulfuron,

KUH 911, KUH 920 lactofen, lenacil, linuron, LS830556,

MCPA, MCPA-thioethyl, MCPB, mecoprop, mecoprop-P, mefenacet, mefluidide, metam, metamitron, metazachlor, methabenzthiazuron, methazole, methoroptryne, methyldymron, methyl isothiocyanate, metobromuron, metoxuron, metribuzin, metsulfuron, molinate, monalide, monolinuron, MSMA, metolachlor, metosulam, metobenzuron, napropanilide, napropamide, naptalam, neburon, nicosulfuron, norflurazon, sodium chlorate, oxadiazon, oxyfluorfen, orbencarb, oryzalin, quinchlorac, quinmerac, propyzamide, prosulfocarb, pyrazolate, pyrazolsulfuron, pyrazoxyfen, pyributicarb, pyridate, paraquat, pebulate, pendimethalin, pentachlorophenol, pentanochlor, petroleum oils, phenmedipham, picloram, piperophos, pretilachlor, primisulfuron, prodiamine, prometryn, propachlor, propanil, propaquizafob, propazine, propham, pyrithiobac, quinmerac, quinocloamine, quizalofop, quizalofop-P, rimsulfuron sethoxydim, sifuron, simazine, simetryn, sulfometuron, sulfentrazone, sulcotrione, sulfosate, tar oils, TCA, tebutam, tebuthiuron, terbacil, terbumeton, terbuthylazine, terbutryn, thiazafluoron, thifensulfuron, thiobencarb, thiocarbazil, tralkoxydim, triallate, triasulfuron, tribenuron, triclopyr, tridiphane, trietazine, trifluralin, tycor, thdiazimin, thiazopyr, triflusulfuron, vernolate.

The weight ratios of the active compounds in these active compound combinations can be varied within relatively large ranges.

The combinations of active compounds preferably obtain the active compound in an amount of from 0.1 to 99.9%, in particular from 1 to 75%, particularly preferably from 5 to 50%, the remainder up to 100% being made up by one or more of the abovementioned co-components.

The microbicidal compositions or concentrates used for protecting industrial materials comprise the active compound or the active compound combination in a concentration of from 0.01 to 95% by weight, in particular from 0.1 to 60% by weight.

The use concentrations of the active compounds or the active compound combinations to be used depends on the kind and the occurrence of the microorganisms to be controlled and on the composition of the material to be protected. The optimum application rate can be determined by test series. The use concentrations are generally in the range of from 0.001 to 5% by weight, preferably of from 0.05 to 1.0% by weight, based on the material to be protected.

The active compounds or compositions according to the invention allow, in an advantageous manner, the replacement of the microbicidal compositions which are currently available by more effective compositions. They have good stability and, in an advantageous manner, a wide activity spectrum.

The examples below serve to illustrate the invention. The invention is not limited to the examples.

EXAMPLE 1

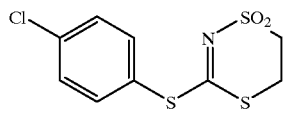

4.97 g (0.024 mol) of 1,1-dioxo-(1,4,2)dithiazinane-3-thione sodium salt are initially charged in 26 ml of $H_2O$ and 130 ml of acetone and cooled to 0° C. The diazonium salt solution I is added dropwise over a period of 8 min. to this mixture. The mixture is initially stirred at 0° C. for 0.5 h and then at room temperature for 2 h. The mixture is extracted with $CH_2Cl_2$, and the organic phase is washed with 1N HCl and $H_2O$, dried and concentrated. The residue is chromatographed over silica gel.

Yield 2.6 g ((=)÷% of theory).

m.p.:=166° C.

Diazonium salt solution I 4.97 g (0.024 mol) of 4-chloroaniline are initially charged in 46.8 ml of $H_2O$ and 6.5 ml of HCl (conc.), cooled to 0° C., and a solution of 1.9 g of $NaNO_2$ in 15.6 ml of $H_2O$ is added dropwise. The mixture is stirred for 1 h and adjusted to pH 4.5 using 6.3 g of sodium acetate.

The compounds of the formula (I) listed in Table 1 are prepared in a similar manner.

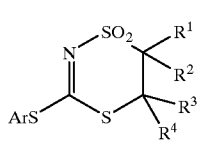
(I)

TABLE 1
| Ex. No. | R¹ | R² | R³ | R⁴ | Ar | Physical constants |
|---|---|---|---|---|---|---|
| 1 | H | H | H | H |  | m.p. = 166° C. |
| 2 | H | H | H | H | 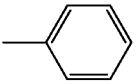 | m.p. = 143° C. |
| 3 | H | H | H | H | 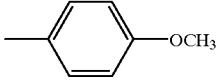 | m.p. = 152° C. |
| 4 | H | H | H | H | 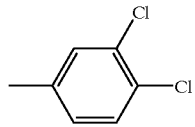 | m.p. = 175° C. |
| 5 | H | H | H | H | 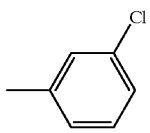 | m.p. = 136° C. |
| 6 | H | H | H | H | 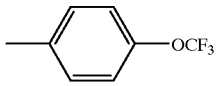 | m.p. = 124° C. |
| 7 | H | H | H | H | 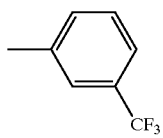 | m.p. = 128° C. |
| 8 | H | H | H | H | 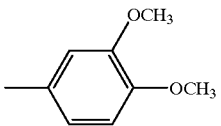 | m.p. = 184° C. |
| 9 | H | H | H | H | 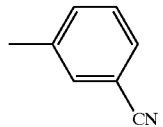 | m.p. = 179° C. |
| 10 | H | H | H | H | 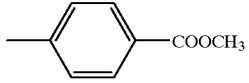 | m.p. = 161° C. |
| 11 | H | H | H | H | 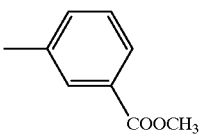 | m.p. = 132° C. |

TABLE 1-continued

| Ex. No. | R¹ | R² | R³ | R⁴ | Ar | Physical constants |
|---|---|---|---|---|---|---|
| 12 | H | H | H | H | 2-NO₂-phenyl | m.p. = 162° C. |
| 13 | H | H | H | H | 4-NO₂-phenyl | m.p. = 166° C. |
| 14 | H | H | H | H | 4-F-phenyl | ¹H-NMR (CDCl₃) δ = 3.37 (2H, m), 3.57 (2H, m), 7.16 (2H,d), 7.55 (2H,d) |
| 15 | H | H | H | H | 2,4-Cl₂-phenyl | ¹H-NMR (CDCl₃) δ = 3.44 (2H, m), 3.61 (2H, m), 7.4–7.5 (2H, m), 7.65 (1H,d). |
| 16 | H | H | H | H | 4-phenoxy-phenyl | ¹H-NMR (CDCl₃/DMSO) δ = 3.45 (2H, m), 3.59 (2H, m), 7.0–7.8 (9H, m) |
| 17 | H | H | H | H | 4-CN-phenyl | ¹H-NMR (CDCl₃) δ= |
| 18 | H | H | H | H | 2-COOCH₃-phenyl | Oil |

Use Example A

To demonstrate the efficacy against fungi, the minimum inhibitory concentrations (MIC) of agents according to the invention are determined:

An agar which is prepared using malt extract is admixed with active compounds according to the invention at concentrations of from 0.1 mg/l to 5,000 mg/l. After the agar has solidified, it is contaminated with pure cultures of the test organisms listed in Table 2. The MIC is determined after 2 weeks of storage at 28° C. and from 60 to 70% relative atmospheric humidity. The MIC is the lowest concentration of active compound at which no colonization by the microbial species used is observed, it is stated in Table 2 below.

TABLE 2

Minimum inhibitory concentrations (ppm) of compounds of the formula (I) according to the invention

| Example No. | 1 | 2 | 5 |
|---|---|---|---|
| *Penicillium brevicaule* | <40 | <40 | <40 |
| *Chaetomium globosum* | <40 | <40 | <40 |
| *Aspergillus niger* | <40 | 200 | <40 |

We claim:
1. A compound of the general formula (I)

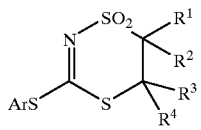

wherein
$R^1$, $R^2$, $R^3$, $R^4$ independently of one another each represent hydrogen, unsubstituted or substituted alkyl, alkenyl, alkynyl or aryl
Ar represents unsubstituted or substituted aryl.

2. A compound of the formula (I) according to claim 1, wherein
$R^1$, $R^2$, $R^3$ and $R^4$ independently of one another each represent hydrogen, straight-chain or branched alkyl having 1 to 10 carbon atoms, straight-chain or branched alkenyl having 2 to 10 carbon atoms or straight-chain or branched alkynyl having 2 to 10 carbon atoms, which is unsubstituted or mono- to polysubstituted by identical or different substituents selected from the group consisting of halogen, alkoxy having 1 to 6 carbon atoms, halogenoalkoxy having 1 to 6 carbon atoms and 1 to 9 identical or different halogen atoms, alkylthio having 1 to 6 carbon atoms, halogenoalkylthio having 1 to 6 carbon atoms and 1 to 9 identical or different halogen atoms, acyl having 1 to 6 carbon atoms, acyloxy having 1 to 6 carbon atoms, alkoxy carbonyl having 1 to 6 carbon atoms, amino, which is unsubstituted or substituted by identical or different substituents selected from the group consisting of alkyl and aryl, which is unsubstituted or substituted by phenoxy, aryl, pyridyl or pyridyloxy, nitro or cyano, or represent aryl, which is unsubstituted or mono- to pentasubstituted by halogen, alkyl having 1 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino having straight-chain or branched alkyl having 1 to 6 carbon atoms, dialkylamino having identical or different, straight-chain or branched alkyl having in each case 1 to 6 carbon atoms, cycloalkyl having 1 to 6 carbon atoms, methylenedioxy, difluoromethylenedioxy, chlorofluoromethylene-dioxy, dichloromethylenedioxy, nitro or cyano
and
Ar represents aryl,
which is unsubstituted or mono- to pentasubstituted by halogen, alkyl having 1 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino having a straight-chain or branched alkyl having 1 to 6 carbon atoms, dialkylamino having identical or different, a straight-chain or branched alkyl having in each case 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano.

3. A compound of the formula (I) according to claim 1, wherein
$R^1$, $R^2$, $R^3$ and $R^4$ independently of one another each represent hydrogen, straight-chain or branched alkyl having 1 to 8 carbon atoms, straight-chain or branched alkenyl having 2 to 8 carbon atoms or straight-chain or branched alkynyl having 2 to 8 carbon atoms, which is unsubstituted or mono- to tetrasubstituted by identical or different substituents selected from the group consisting of fluorine, chlorine, alkoxy having 1 to 5 carbon atoms, halogenoalkoxy having 1 to 5 carbon atoms and 1 to 5 halogen atoms selected from the group consisting of fluorine and chlorine atoms, alkylthio having 1 to 5 carbon atoms, halogenoalkylthio having 1 to 5 carbon atoms and 1 to 5 halogen atoms selected from the group consisting of fluorine and chlorine atoms, acyl having 1 to 5 carbon atoms, acyloxy having 1 to 5 carbon atoms, alkoxycarbonyl having 1 to 5 carbon atoms, amino, which is unsubstituted or substituted by identical or different substituents selected from the group consisting of alkyl having 1 to 4 carbon atoms and phenyl, which is unsubstituted or substituted by phenoxy, aryl, pyridyl, pyridyloxy, nitro or cyano, or represent phenyl, which is unsubstituted or mono- to tetrasubstituted by fluorine, chlorine, alkyl having 1 to 8 carbon atoms, halogenoalkyl having 1 to 6 carbon atoms and 1 to 6 halogen atoms selected from the group consisting of fluorine and chlorine atoms, alkoxy having 1 to 8 carbon atoms, halogenoalkoxy having 1 to 6 carbon atoms and 1 to 6 halogen atoms selected from the group consisting of fluorine and chlorine atoms, alkylthio having 1 to 8 carbon atoms, halogenoalkylthio having 1 to 6 carbon atoms and 1 to 6 halogen atoms selected from the group consisting of fluorine and chlorine atoms, amino, monoalkylamino having alkyl radicals of 1 to 4 carbon atoms, dialkylamino having identical or different alkyl radicals having in each case 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano,
and
Ar represents phenyl, which is unsubstituted or mono- to tetrasubstituted by fluorine, chlorine, bromine, alkyl having 1 to 8 carbon atoms, halogenoalkyl having 1 to 6 carbon atoms and 1 to 6 halogen atoms selected from the group consisting of fluorine and chlorine atoms alkoxy having 1 to 8 carbon atoms, halogenoalkoxy having 1 to 6 carbon atoms and 1 to 6 halogen atoms selected from the group consisting of fluorine and chlorine atoms, alkythio having 1 to 8 carbon atoms, halogenoalkylthio having 1 to 6 carbon atoms and 1 to 6 halogen atoms selected from the group consisting of fluorine and chlorine atoms, amino, monoalkylamino having alkyl radicals of 1 to 4 carbon atoms, dialkylamino having identical or different alkyl radicals having in each case 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano.

4. A pesticidal composition comprising at least one compound of the formula (I) according to claim 1 and one or more extenders and/or surfactants.

5. A process for controlling pests, comprising the step of allowing a compound of the formula (I) according to claim 1 to act on pests and/or their habitat.

6. A process for preparing a pesticidal composition comprising the step of mixing a compound of the formula (I) according to claim 1 with extenders and/or surfactants.

7. A process for preparing a compound of the formula (I)

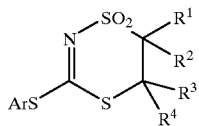

(I)

wherein
R¹, R², R³ and R⁴ independently of one another each represent hydrogen, unsubstituted or substituted alkyl, alkenyl, alkynyl or aryl and
Ar represents unsubstituted or substituted aryl,
comprising the step of reacting a salt of the general formula (II)

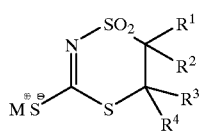

(II)

wherein
R¹, R², R³ and R⁴ are each as defined above and
M$^{\oplus}$ represents an alkali metal ion or alkaline earth metal ion,
with a diazonium salt of the general formula (III)

$$Ar\!-\!N\!\equiv\!N^{\oplus}A^{\ominus} \qquad (III)$$

wherein
Ar is as defined above and
A$^{\ominus}$ represents an anion of a mineral acid, in an aqueous/alkaline solution.

8. The process of claim 7 wherein M is selected from the group consisting of Na⁺ and K⁺.

9. The process of claim 7 wherein the reaction is carried out in the presence of a catalyst.

10. A process for preparing a pesticidal composition, comprising the step of mixing a compound of the formula (I) according to claim 2 with extenders and/or surfactants.

11. A process for preparing a pesticidal composition, comprising the step of mixing a compound of the formula (I) according to claim 3 with extenders and/or surfactants.

12. A process for preparing a pesticidal composition, comprising the step of mixing a pesticidal composition of formula (I) according to claim 4 with extenders and/or surfactants.

* * * * *